United States Patent
Hay et al.

(10) Patent No.: US 6,325,765 B1
(45) Date of Patent: Dec. 4, 2001

(54) METHODS FOR ANALYZING EYE

(76) Inventors: S. Hutson Hay, 310 Clinton Ave. West, Huntsville, AL (US) 35810; Herbert U. Fluhler, 340 Usher Rd., Madison, AL (US) 35758

(*) Notice: Subject to any disclaimer, the term of this patent is extended or adjusted under 35 U.S.C. 154(b) by 0 days.

(21) Appl. No.: 09/549,762

(22) Filed: Apr. 14, 2000

Related U.S. Application Data

(63) Continuation-in-part of application No. 09/150,000, filed on Sep. 8, 1998, now Pat. No. 6,095,989, which is a continuation-in-part of application No. 08/932,036, filed on Sep. 17, 1997, now abandoned, which is a continuation-in-part of application No. 08/863,801, filed on May 27, 1997, now abandoned, which is a continuation-in-part of application No. 08/324,884, filed on Oct. 18, 1994, now Pat. No. 5,632,282, which is a continuation-in-part of application No. 08/093,685, filed on Jul. 20, 1993, now Pat. No. 5,355,895.

(51) Int. Cl.$^7$ ...................................... A61B 5/00
(52) U.S. Cl. .......................................... 600/558
(58) Field of Search ........................... 600/558; 351/200, 351/221

(56) References Cited

U.S. PATENT DOCUMENTS

| | | | |
|---|---|---|---|
| 4,569,354 | * 2/1986 | Shapiro et al. | 128/665 |
| 5,139,030 | * 8/1992 | Seay | 600/559 |
| 5,303,709 | * 4/1994 | Dreher et al. | 128/665 |
| 5,355,895 | * 10/1994 | Hay | 600/559 |
| 5,632,282 | * 5/1997 | Hay et al. | 600/559 |

* cited by examiner

*Primary Examiner*—Max Hindenburg
(74) *Attorney, Agent, or Firm*—Mark Clodfelter

(57) ABSTRACT

A method for analyzing a retinal reflection that may be of less than optimum quality is disclosed. In the event an image of a retinal reflex taken by a retinal photometer is of low contrast or have certain other degradations, then matched filter tests applied to portions of the image containing the eyes may be performed in order to locate the retinal reflex. For determining potential eye abnormalities, a plurality of intensity shape determination tests may be performed, these including comparisons of the eyes against a center of gravity of the shape distribution, a least-squares fit and an analysis of the moments of Hu (of the retinal reflex) converted to Zernike polynomials. A Hirshberg deviation test is performed to determine if one or the other, or both, of the eyes are deviating. Intrasymmetry and intersymmetry of the reflex are analyzed to indicate cataracts, differences of optical power and other similar problems.

17 Claims, 13 Drawing Sheets

METHODS FOR ANALYZING EYE

CROSS REFERENCES TO RELATED APPLICATIONS

This application is a continuation-in-part of patent application Ser. No. 09/150,000, filed Sept. 8, 1998 now U.S. Pat. No. 6,095,989 which is a continuation-in-part of patent application Ser. No. 08/932,036, filed Sept. 17, 1997, now abandoned, and which is a continuation-in-part of patent application Ser. No. 08/863,801, filed May 27, 1997, now abandoned, and in turn a continuation-in-part of patent application Ser. No. 08/324,884, filed Oct. 18, 1994, now U.S. Pat. No. 5,632,282, which is a continuation-in-part of patent application Ser. No. 08/093,685, filed Jul. 20, 1993, now U.S. Pat. No. 5,355,895.

FIELD OF THE INVENTION

Improved methods for locating the pupil and verifying that a pupil has been located are disclosed. In these methods, a number of matched filter tests are employed, each testing the image array for different light intensity values indicative of structures of an iris and a pupil. Additionally, methods are disclosed for indicating types of defects in eyes of a subject, and in some instances quantification of a degree of the defects is disclosed.

BACKGROUND OF THE INVENTION

In Applicants prior application, a least squares circle fitting is used to estimate the radius of a binary pupil disk mask. Using this radius and a similarly derived radius for the iris, an impulse response array is created and used in a matched filter test to determine whether or not a valid pupil is in the image array.

One problem with this approach is that occasionally a portion of the eye, such as the eyelids and/or the white portion of the eye, may have intensity values below a threshold for creating the binary image mask. This may occur if there is low contrast in the image of the eyes. In this instance, those portions of the binary image of the iris or pupil below the threshold register as missing, which in turn reduces the correlation peak below a level necessary to obtain a detection of the pupil from the correlation peak. This results in the eye not being found.

Accordingly, it is one object of the invention to provide a more robust algorithm for reliably finding the eyes of a subject by using a plurality of matched filter tests that each examine a different part of the eyes. It is another object of the invention to provide indications of magnitude of some disease processes of the eyes. It is a further object of the invention to provide a sense of homeostasis of the eyes. Other objects will become apparent upon a reading of the following specification and appended claims.

SUMMARY OF THE INVENTION

A method for analyzing a retinal reflex is disclosed. Initially, an eye array of a subject is captured by a reflex photometer, after which an eye array is clipped and stored. If the eye array is of low contrast, then a plurality of matched filter tests are performed to locate the eye. In addition, shape determination tests may be performed in an attempt to further locate the eye. After the eye is located, a Hirshberg deviation test is performed to determine of there is any deviation of the eyes from a forward gaze. Symmetry tests may then be performed to ascertain the degree of symmetry of each eye and one eye as compared with the other.

DETAILED DESCRIPTION OF THE DRAWINGS

This application relies on the use of a reflex photometer to digitally capture images of a subject's eyes and retinal reflection, commonly referred to as the retinal reflex. In addition, a general purpose computer coupled to a digital camera of the reflex photometer is programmed to isolate selected features of the reflex, which features being used to locate the pupil and test the located pupil for certain abnormal conditions or disease processes. Such a reflex photometer and related computerized analysis may be found in Applicant's U.S. Pat. Nos. 5,355,895, 5,632,282 and patent application Ser. No. 09/150,000, these two patents and the referenced application being incorporated by reference in their entirety herein.

Figure 2:
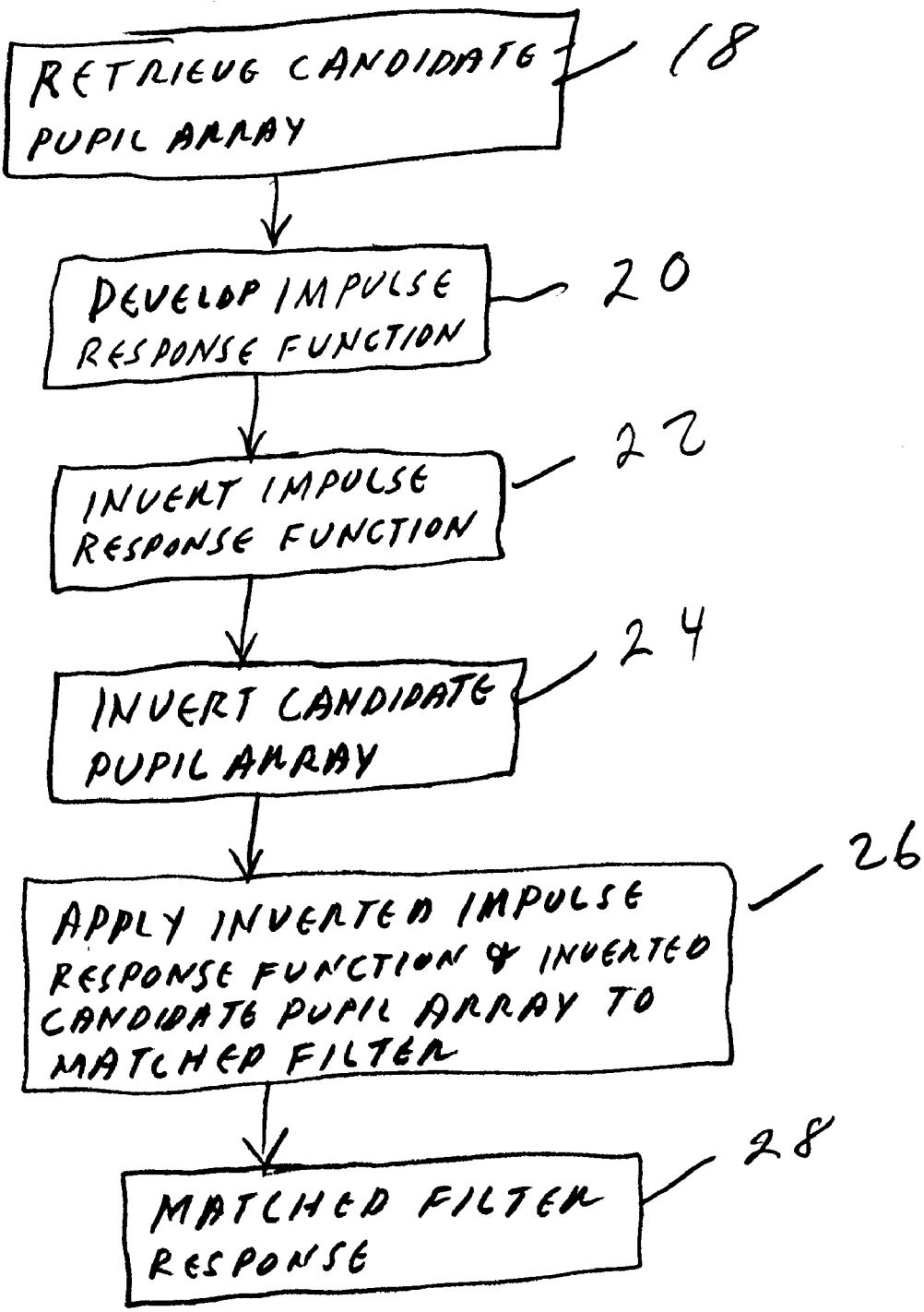
FIG. 2 is a flowchart illustrating logic flow of a method of locating a pupil of a subject.

In the drawings of the instant invention, flowcharts are provided to illustrate logic flow, and diagrams generally illustrating the logic flows are provided in figures designated by the same numeral as the respective flowchart and carrying an additional designation of "a", "b", etc. For instance, the flowchart of FIG. 2 is accompanied by a drawing designated FIG. 2a to illustrate the process of the flowchart of FIG. 2.

Figure 1:
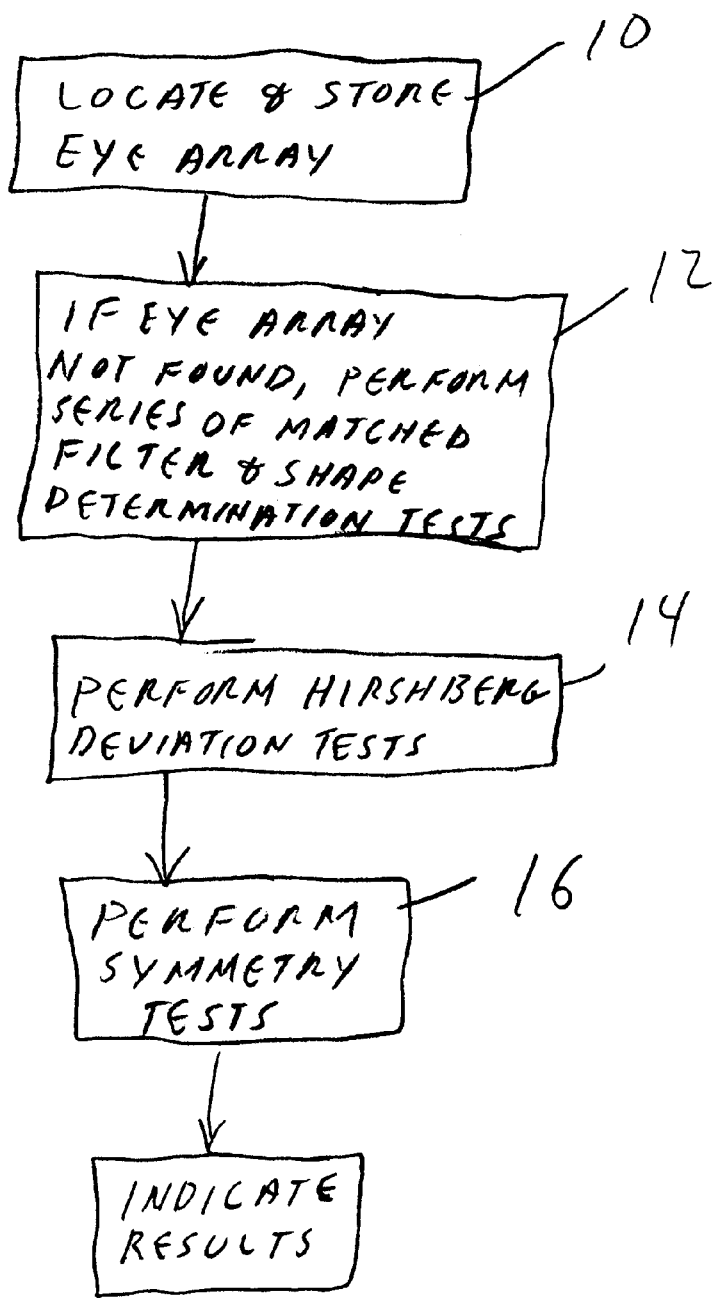
FIG. 1 is a flowchart illustrating logic flow of the system.

Referring initially to FIG. 1, an upper level flowchart of a method for locating and analyzing eyes of a subject is shown. As in the incorporated patents and application, these algorithms may be implemented by a general purpose computer, such as one using a Pentium, Pentium II processor or other compatible processor and at least 32 megs of ram. Any suitable operating system may be used, such as Windows 95/98/2000, an Apple processor and operating system, a Linux based system or others, as determined by one skilled in the art. Also, the quantity of ram memory and hard disk space necessary to efficiently implement the programming would be well within the purview of one skilled in the art.

In the flowchart of FIG. 1, at box 10 an eye array of 128 by 128 pixels is located and stored. At box 12, if the eye array is not found, a series of matched filters and shape determination tests are performed. Typically, the eye or eyes are located reliably by the tests in the incorporated references, but as stated, occasionally an image of an eye is taken wherein there is low contrast or the eye is reported as not being found due to portions of the eye registering intensities below the threshold for creating a binary image mask. Here, at box 12 matched filters are applied to different parts of the eye image, and shape determination tests register the shape of the pupil intensity distribution. This intensity distribution is indicative of a number of disease processes in the eyes. At box 14 the Hirschberg deviation of the eyes is measured, this deviation indicating the severity of any amblyopia that may be present in the subject eyes.

At box 16 a series of symmetry tests are performed, these symmetry tests being useful in determining whether the general condition of the eyes is normal or not. Here, the eyes of a subject are compared against each other, with a greater difference between the eyes indicating greater asymmetry between the eyes.

Figure 2A:
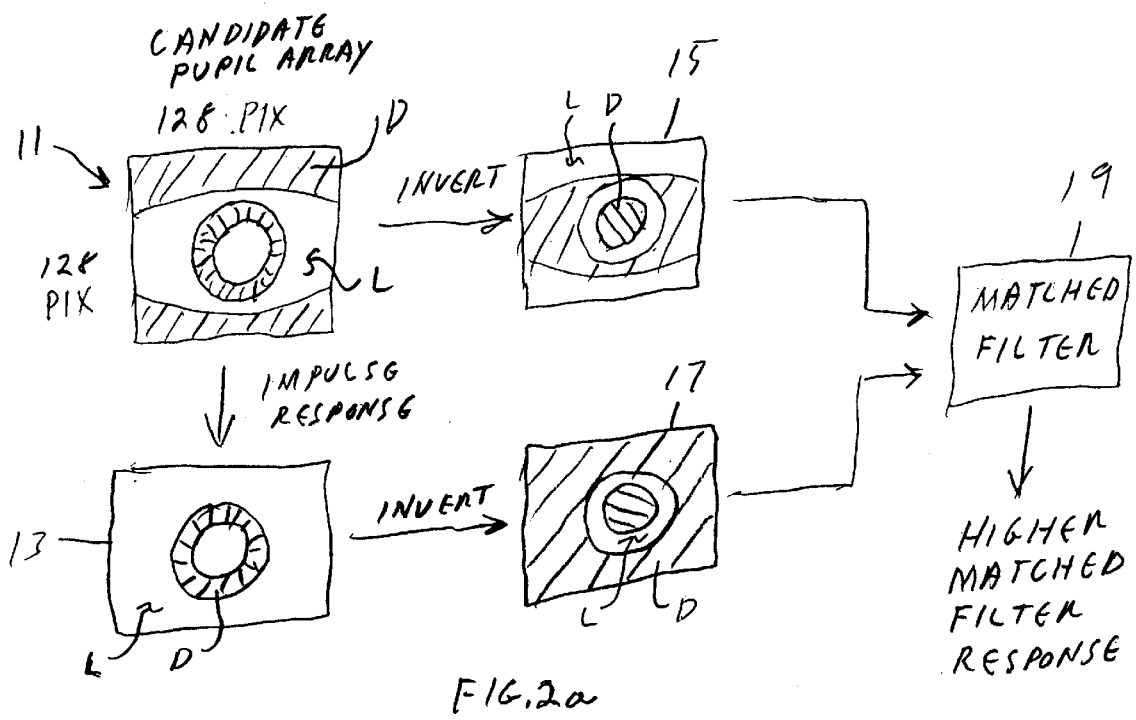
FIG. 2a is a diagram of the logic of FIG. 2.

Referring now to FIG. 2, the process of box 12 of FIG. 1 is delineated. Initially, at box 18, the binary mask of the candidate pupil array is retrieved from memory. As stated, this array may be sized 128 by 128 pixels, and contains a binary image of the eye, which also may include a portion of the eyelids and possibly areas immediately adjacent the eyelids. As described in the incorporated references, this array is a thresholded binary array, with pixels above the threshold being assigned a "1" value and pixels below the threshold being assigned a "0" value, as indicated by dark areas D (pixels assigned a "1" value) and light areas L (pixels assigned a "0" value), as shown in FIG. 2a. If the image is a low contrast image, or if portions of the eye iris or eyelids are not within the cropped image, then a plurality of matched filters are applied to the image. Each of these matched filters looks at different structures in the eyes. At box 20 (FIG. 2) an impulse response function of the candidate array is performed as described in the incorporated references to develop a binary mask 13 (FIG. 2a), and at boxes 22 and 24 the pixels making up the candidate pupil array and impulse response function are inverted to form arrays 15 and 17, respectively. By inverting these binary images, the following matched filter tests are forced or weighed to match more to the iris ring and less on the pupil and eye whites, the pupil and eye whites sometimes being of low contrast. In most instances, this produces a good correlation when the iris and eye whites are of low contrast. At box 26 the inverted impulse response function 17 and the inverted binary image 15 are applied to a matched filter 19, and at box 28 the highest correlation of the matched filter response is obtained.

Figure 3A:
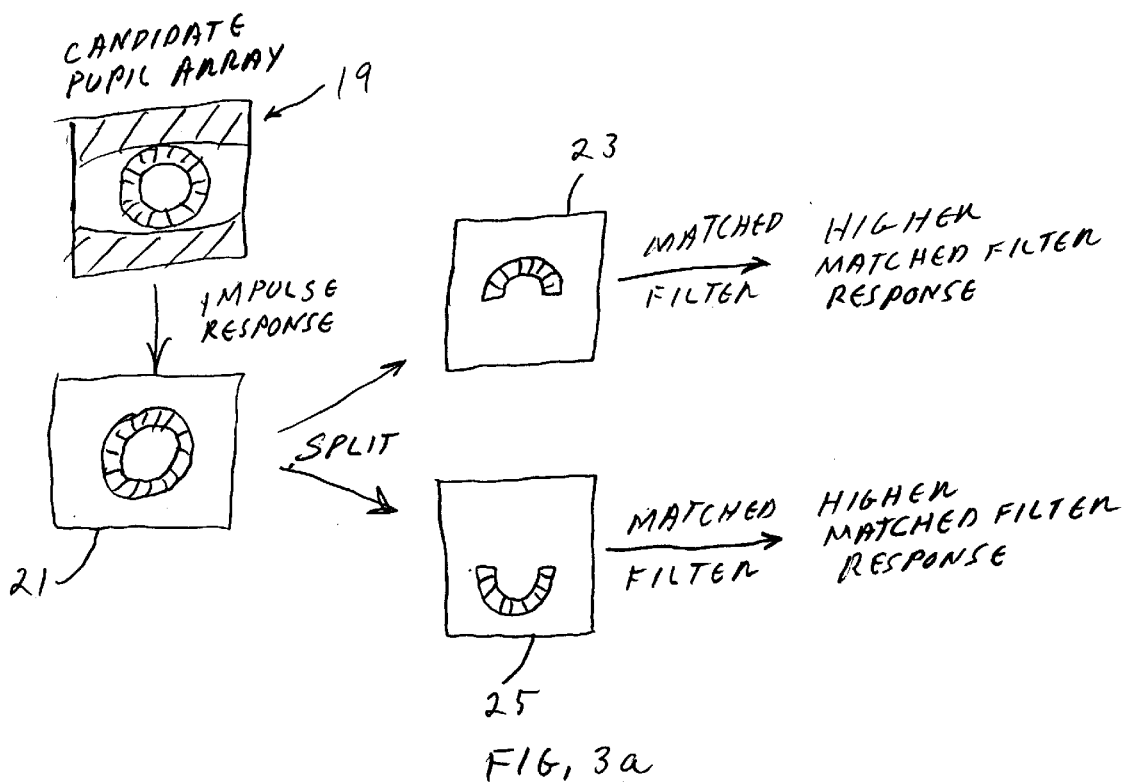
FIG. 3a is a diagram illustrating the logic flow of FIG. 3
Figure 3:
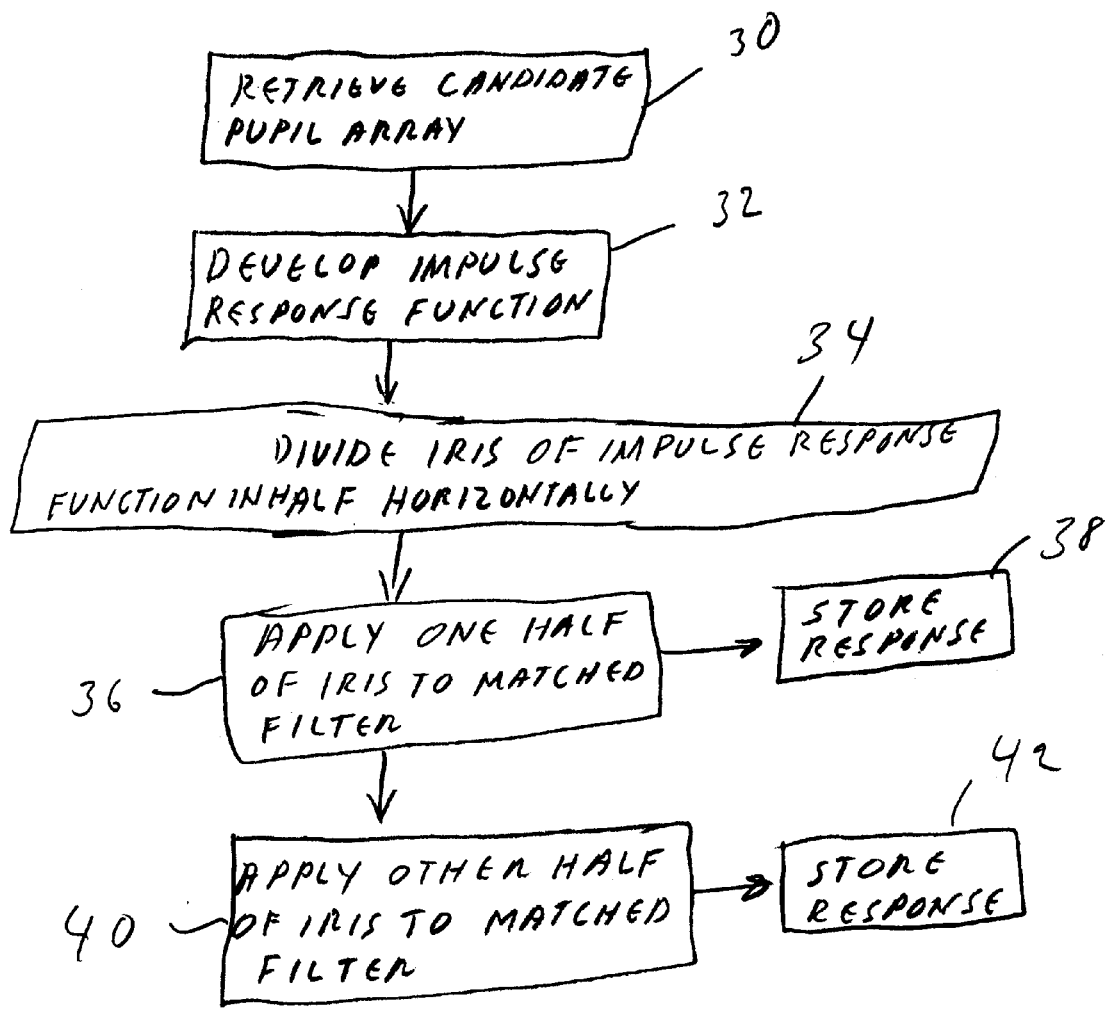
FIG. 3 is a flowchart illustrating logic flow of another method of locating a pupil of a subject.

In FIG. 3 another method is shown for obtaining a good correlation output when portions of the eye image are of low contrast or if portions of the eye are not visible. At box 30 the binary, thresholded pupil array 19 (FIG. 3a) is retrieved, and at box 32 an impulse response function 21 is developed. At box 34 the impulse response function is divided in half horizontally to form arrays 23 and 25, and at box 36 one of the halves, in this example the upper half, of the impulse response function is compared to the candidate eye array in a matched filter test. The highest correlation of this test is stored at box 38. At box 40 the other half (the lower half in this example) is compared in a matched filter test with the candidate binary pupil eye array and the highest correlation stored at box 42. Other similar types of matched filter tests may be performed, such as dividing the impulse response function along a vertical line or diagonal lines to obtain two halves, or taking a mirror image of the impulse response function for comparison with the candidate binary eye array in a matched filter. Conceivably, the impulse response function may also be divided into more than two portions and each portion compared to the candidate pupil binary image in a matched filter test to obtain a highest correlation for that portion. In addition, the divided portions of the impulse response function may be inverted, and the candidate binary eye array inverted, and the inverted portions and inverted eye array compared in a matched filter. Any or all of the matched filters described may be used in decision logic to optimize the probability of detection of the eye.

With respect to analyzing diseases of the eye, the shape of the pupil reflex light intensity distribution may be used as one way of detecting several disease processes of the eyes. In the instance where the degree of hyperopia or myopia is relatively large, an indication of either may be provided by determining the center of gravity of the pupil intensity distribution and relating magnitude of the disease to displacement of the center of gravity of the pupil reflex light intensity distribution from the geometric center of the pupil, as determined by a circle defined by the edge of the pupil.

Figure 4:
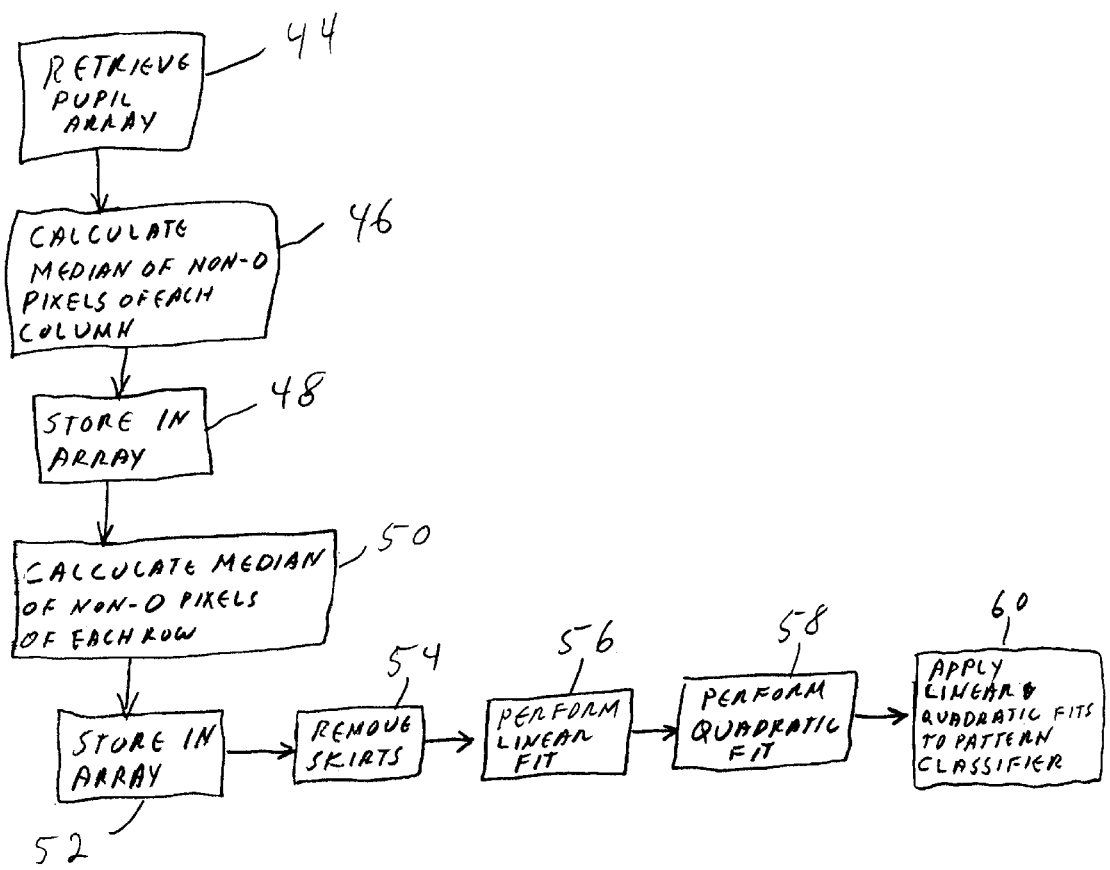
FIG. 4 is a flowchart illustrating logic flow of a method for analyzing light intensity levels of a pupillary reflex.
Figure 4A:
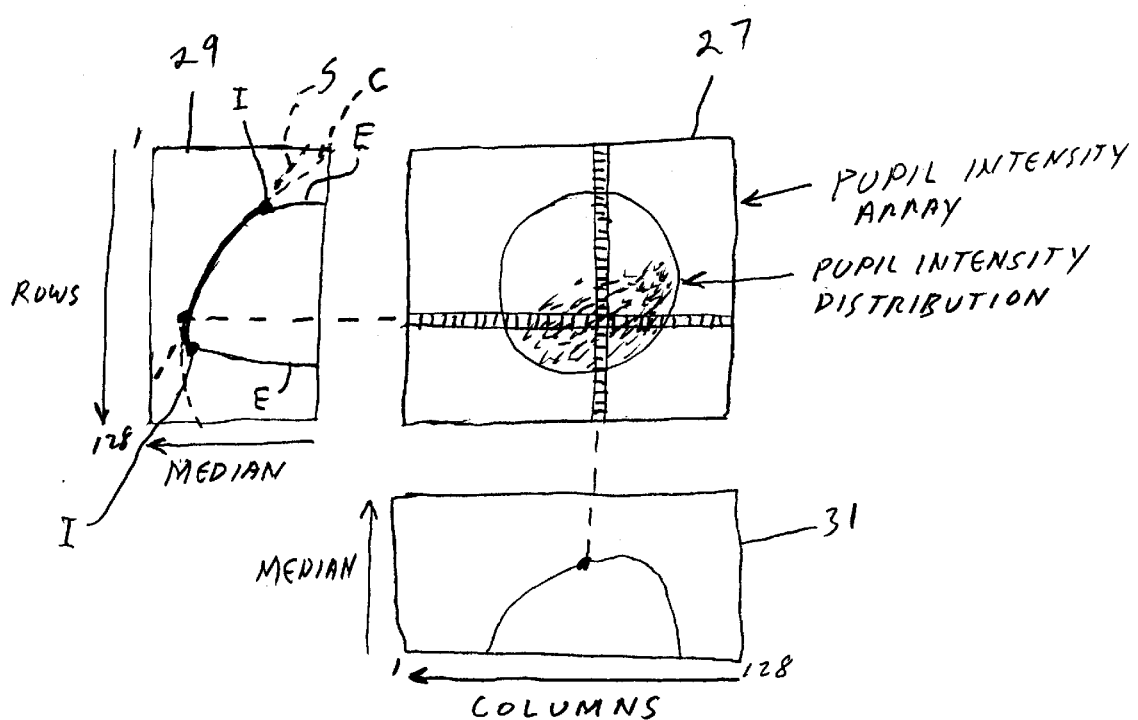
FIG. 4a is a diagram of the logic flow of FIG. 4.

A more detailed measurement of a lessor degree of hyperopia or myopia may be undertaken by a least squares fit of first order and second order polynomials to the median of rows of pixels of the pupil and to the median of columns of pixels of the pupil. Here, and referring to FIGS. 4 and 4a, at box 44 the cropped pupil array 27 is retrieved with its original intensity values, and at box 46 the median value of all non-zero pixels in either columns or rows, in this example columns, of the pupil array is calculated or retrieved. Each of these median values is placed in an array where each position of the array corresponds to a column of the eye array, as shown in FIG. 4a wherein there is a row array 29 and a column array 31. The column array 31 is stored at box 48, and at box 50 the process of calculating median values of non-zero pixels in the other of the rows or columns, in this example the rows, is calculated or retrieved. Each median value is stored at box 52 in a row array 29, and the edges E of the curves developed in the median arrays where the pupil meets the iris are clipped at box 54. This clipping may be accomplished by simply moving in from the pupil edge by a pixel or two, and clipping median values from the edge outward. Another method of clipping may be to determine the inflection points I in the derivative of the curve, and excise points outside the inflection points. In any case, clipping removes the edges of the pupil from consideration in the following analysis so that these edges, which are typically of a sharply different value than the pupil intensity values, do not bias the general intensity distribution of the pupil. The median intensity distributions of the pupil may be subjected to various mathematical fits, such as a linear fit at box 56. Here, a linear fit of the median intensity distribution yields 2 parameters M and B which define a straight line S through the intensity distribution, this line defined by the linear equation $Y=MLX+B$. In a least squares fit sense, this line will generally fit intensity distributions wherein hyperopia or myopia is relatively weak. Additionally, the sign of the value ML indicates whether myopia or hyperopia is present, if positive then myopia is evident, if negative then hyperopia is present.

If a larger degree of hyperopia or myopia is present, then the median intensity distribution becomes curved, which is more easily defined by a quadratic equation utilizing the values Q, M and B to form the equation $Y=QX2+MX+B$ defining a curve C through the intensity distribution, as shown at box 58. In this instance, the quadratic fit will define the shape of curved line C, i.e. whether the curve is convex or concave. As such, the linear fit may be used to characterize the global slope of the median intensity distribution and the quadratic fit may be used to define the shape of the curve. The parameters of these equations may be fed to a pattern classifier at box 60 to measure the degree of myopia or hyperopia present in the pupil. Here, if Q is near zero, the shape of the intensity distribution is nearly flat, indicating mild degrees of hyperopia or myopia. As stated, if ML is positive then myopia is indicated, and if negative then hyperopia is indicated. If ML is of a moderate value and Q is near zero then the myopia or hyperopia is moderate. If ML is moderate and Q is large then the myopia or hyperopia is strong. The actual numeric values for determining hyperopia and myopia are a function of the particular instrument used, and best determined when developing the pattern classifier using truth data.

Figure 5:
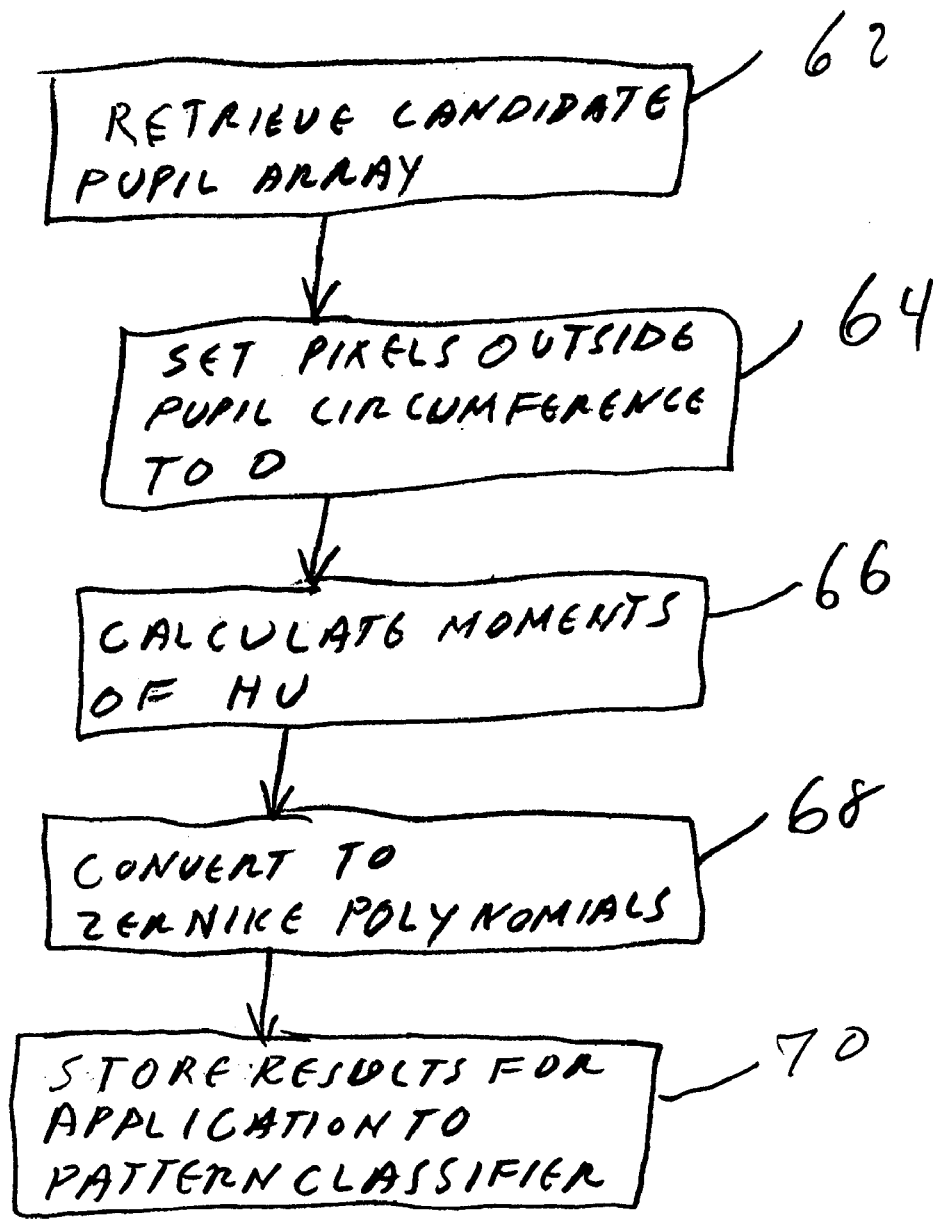
FIG. 5 is a flowchart illustrating logic flow of another method of analyzing light intensity levels of a pupillary reflex.

FIG. 5 shows a flowchart of another analysis wherein the moments of Hu are calculated, and converted to Zernike polynomials which then may be used in a pattern classifier. At box 62 the candidate pupil array is retrieved, and at box 64 the pixel intensity values outside the pupil are set to zero. This eliminates the pixels outside the pupil from consideration in the moments of Hu calculations. The moments of Hu are a set of scalar parameters descriptive of a 2 dimensional image, and which do not change as the image is scaled or rotated. As such, the moments of Hu are representative of the shape of the pupil intensity distribution, and are calculated at box 66. One disadvantage of using the moments of Hu calculations is that they are generally very large numbers. Another disadvantage is that they are not independent, meaning that when one changes, the others change. For these reasons, the moments of Hu are converted to Zernike polynomials at box 68. These polynomials may then be applied to a pattern recognition classifier at box 70 in order to identify and quantify certain diseases of the eyes, such as hyperopia, myopia and cataracts.

Figure 6:
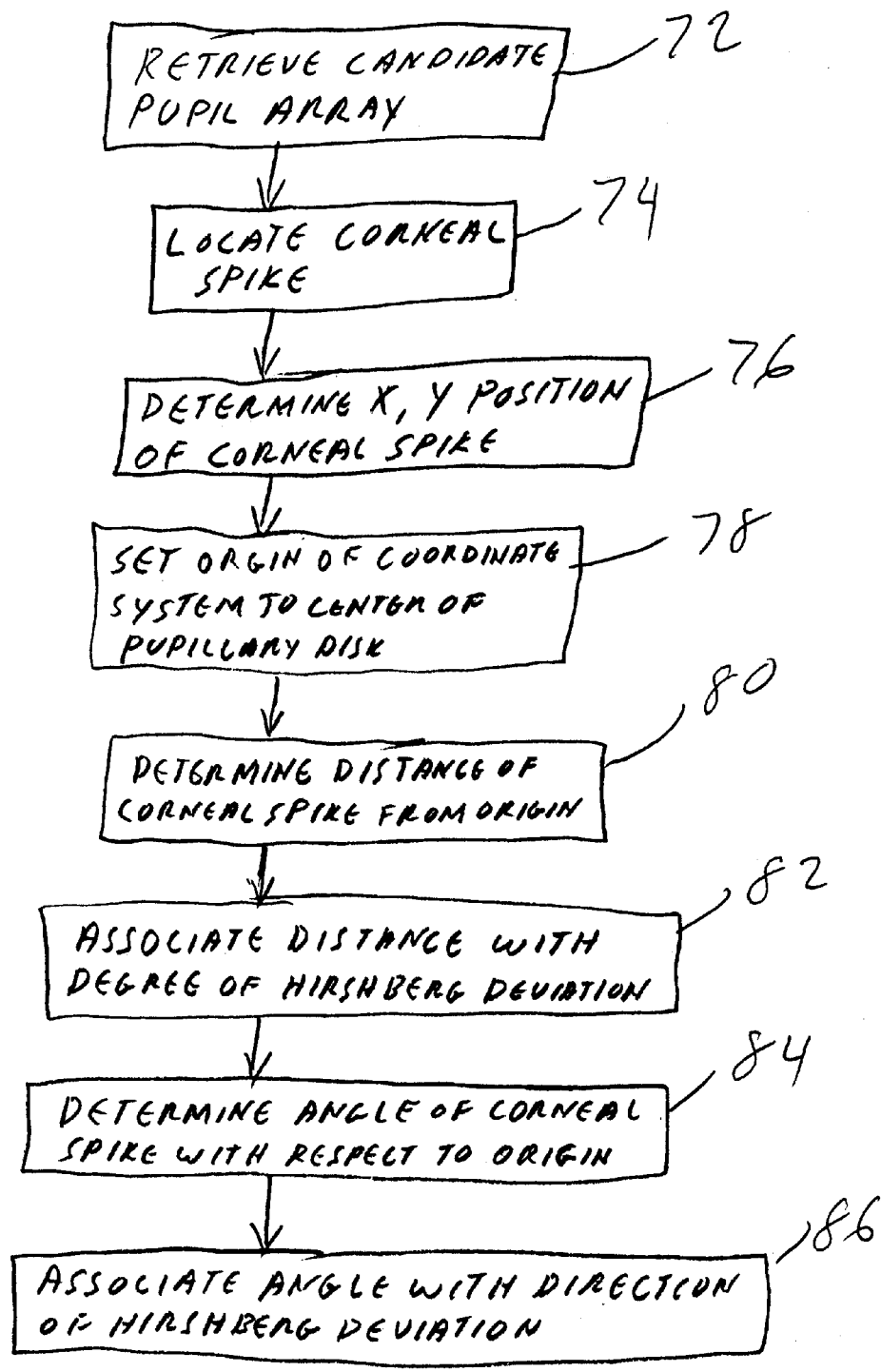
FIG. 6 is a flowchart illustrating logic flow of a method for analyzing location of a corneal reflection.
Figure 6A:
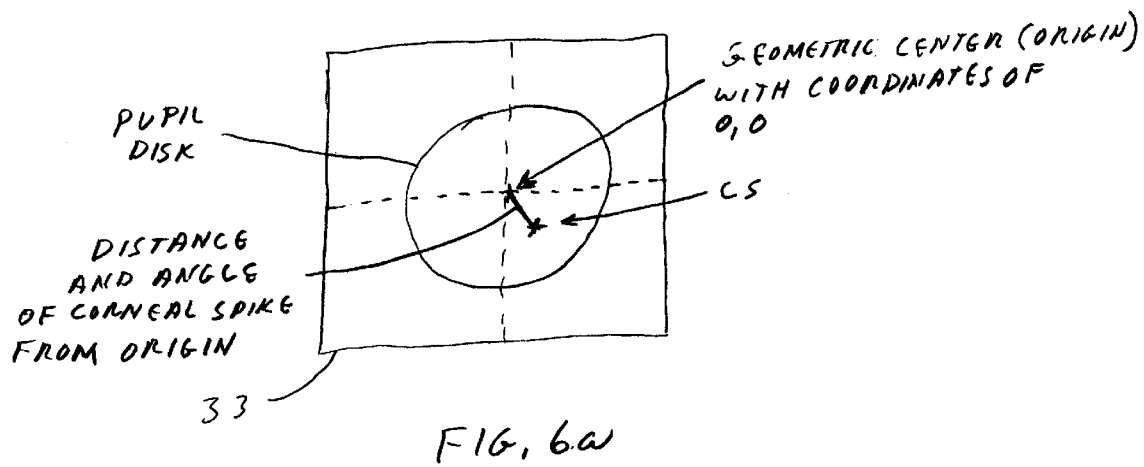
FIG. 6a is a diagram of the logic flow of FIG. 6.

FIG. 6 is a flowchart for determining whether Hirschberg deviation is present in the eye. As stated, this is a condition related to binocular vision where one eye deviates in direction with respect to the other eye. Typically, the deviating eye does not actively see the object of interest the other eye is looking at.

Prior to imaging the eyes in order to determine the Hirshberg deviation, the subject is instructed to look at a target in order to image the eyes in their normal, pointed and focussed position. This may be done by instructing the subject to look directly at the moving lights so that the camera records an image of the eyes in the described angularly offset orientation with respect to the beam of light. In FIG. 6, at box 72, the candidate pupil 33 from this imaging process is retrieved, and at box 74 the corneal spike CS is located as by any of the methods as described in the incorporated references. At boxes 76 and 78, the position of the corneal spike is determined by imposing a coordinate system on the pupil wherein the center of the pupil disk is designated as the origin (0,0 coordinates), and the location of the corneal spike CS is defined in terms of its x, y position in the coordinate system. At box 80 the distance of the corneal spike from the center is determined, and at box 82 this distance is associated with a degree of magnitude of the deviation. At box 84 the angle of the corneal spike with respect to the axes of the coordinate system is determined, and at box 86 this angle is associated with direction of the deviation.

Figure 7:
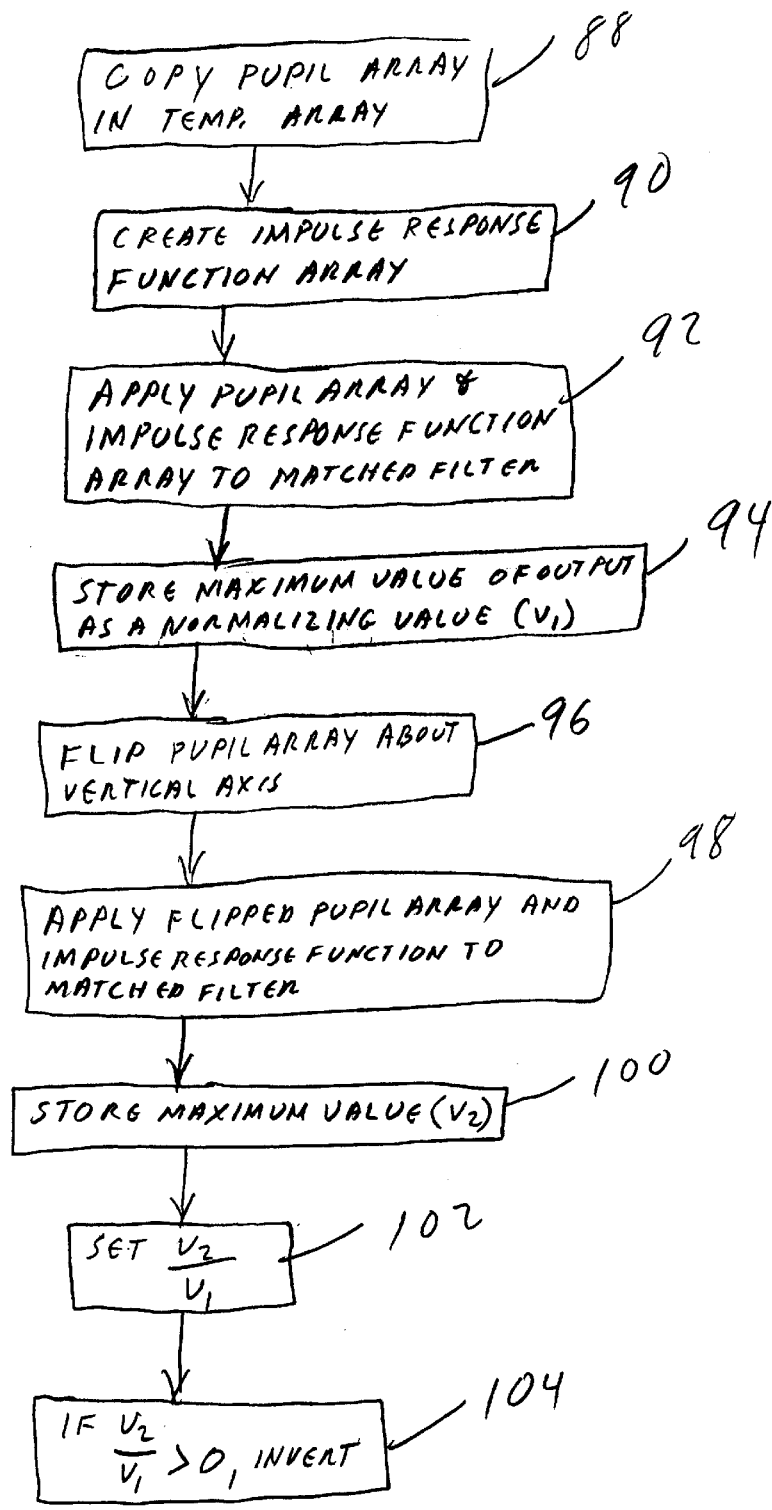
FIG. 7 is a flowchart illustrating logic flow of a method for analyzing binocular vision of a subject.
Figure 7A:
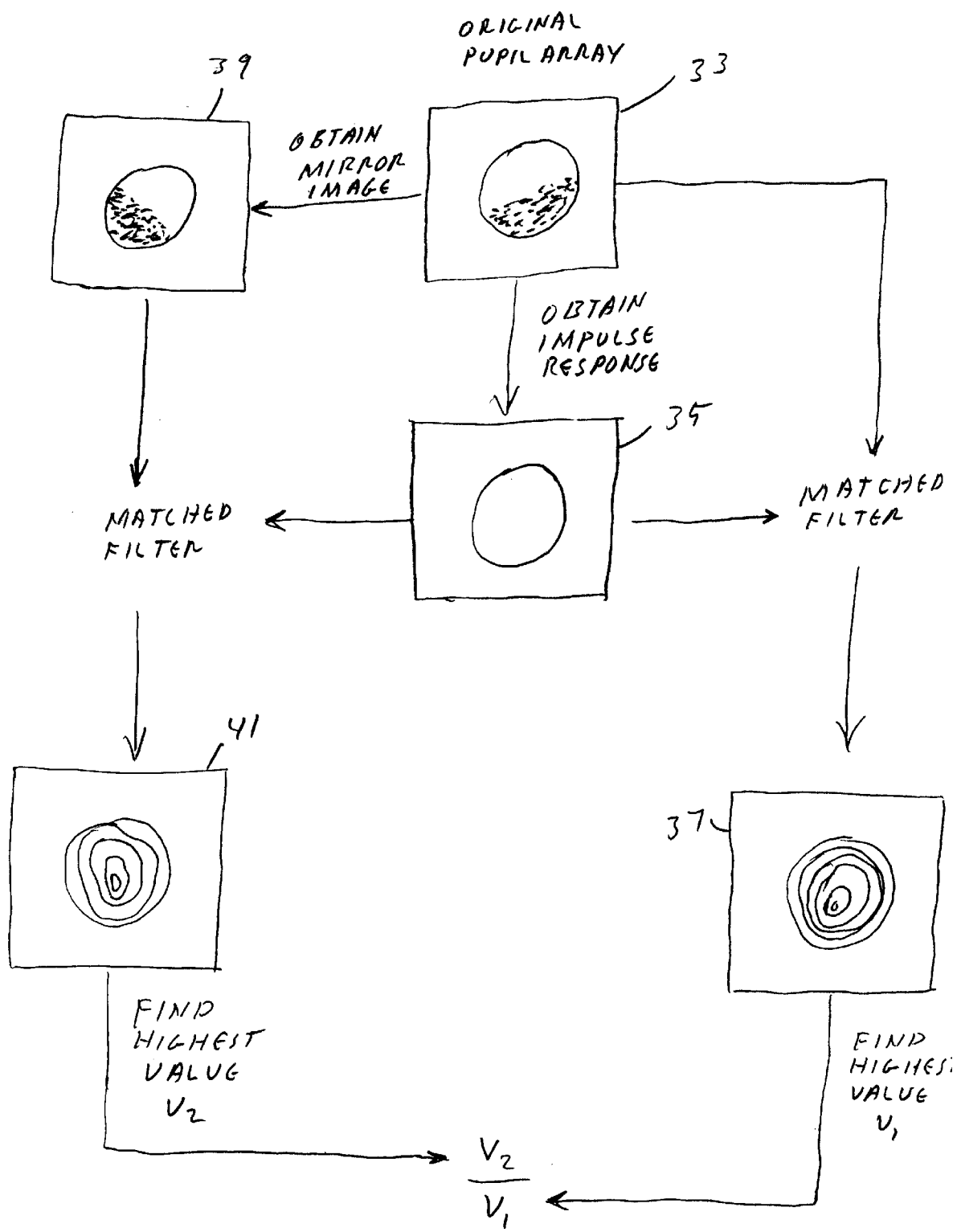
FIG. 7a is a diagram of the logic flow of FIG. 7.

FIGS. 7 and 7*a* illustrate an example of a method for determining whether the eyes of a subject are normal or contain abnormal features we call intra-symmetry. Intra-symmetry is a value between 0 and 1, and is an indication of symmetry of the intensity distribution of the pupil about an axis. Typically, the vertical axis is used, which provides a measure of how similar the right side of the pupil is to the left side. Here, normal eyes or eyes that are hyperoptic or myoptic will give a symmetry value close to 1, while astigmatic eyes or an eye with a cataract will return a value significantly less than 1. While the vertical axis is used in this example, it should be apparent that the horizontal or other axes may be used. Also, testing for symmetry about two different axes would eliminate the possibility of a defect symmetrical with a single axis indicating a symmetrical eye. For example, where symmetry about a vertical axis is used, an eye with either hyperopia or myopia without astigmatism may be determined to be symmetrical. However, if the test for symmetry about a horizontal axis is added, then an asymmetrical eye would be indicated.

As shown in FIGS. 7 and 7*a*, at box 88, the pupil array 33 (with intensity information) is copied into a temporary array and at box 90 an impulse response function is performed to develop an impulse response array 35. The impulse response function and the pupil array 33 are applied to a matched filter at box 92 to develop a matched filter array 37, and the highest result of the matched filter, which is a correlation, is stored for use as a normalizing value V1 at box 94. At box 96 the pupil array is flipped about the vertical axis in order to obtain a mirror image array 39 of the pupil array, and at box 98 the mirror image array 39 and impulse response function array 35 are applied to a matched filter to obtain a matched filter array 41. The maximum result of this matched filter is stored as a value V2 at box 100. At box 102 the value V2 is divided by V1, and if the resulting number is greater than 0 it is inverted at box 104. This value is the intra-symmetry value, and if significantly less than 1, then astigmatism or cataracts are indicated. The intra-symmetry value may also be indicative of non-circular pupils or exo/esotrophias.

Figure 8:
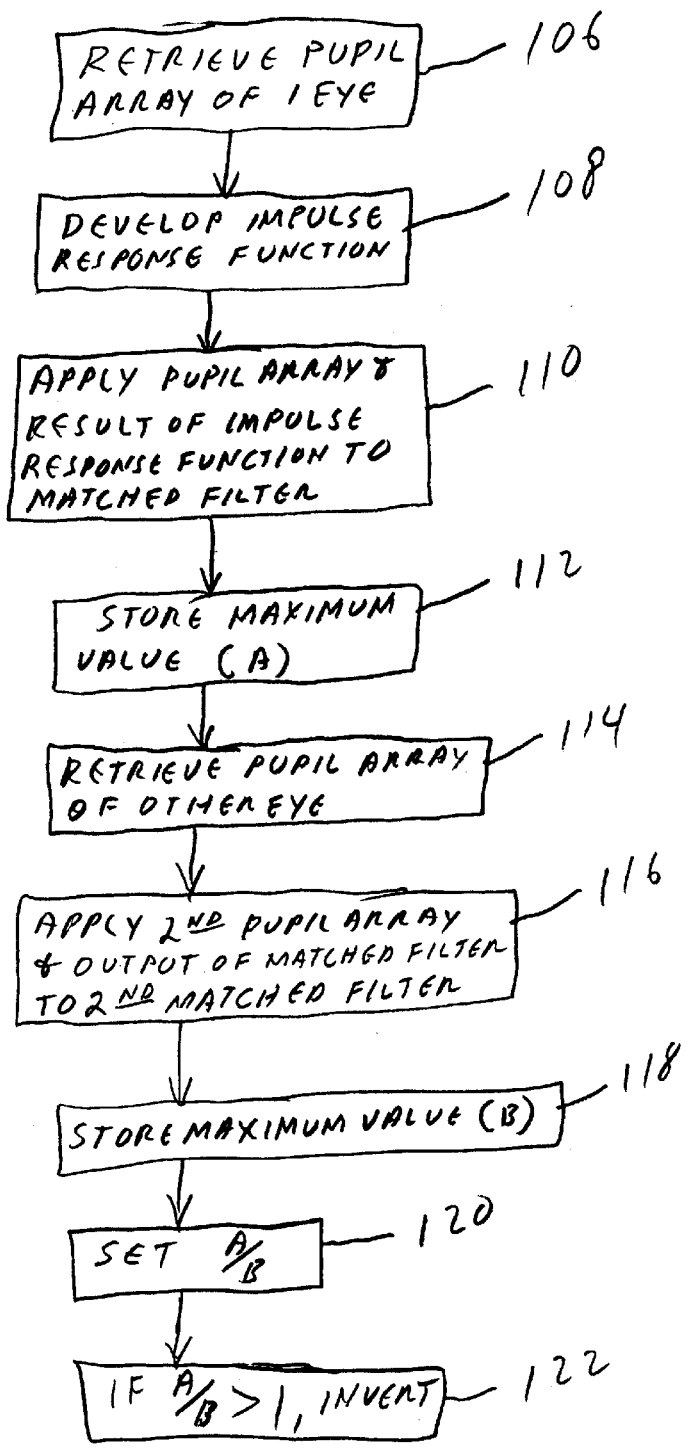
FIG. 8 is a flowchart illustrating logic flow of another method for analyzing binocular vision of a subject.
Figure 8A:
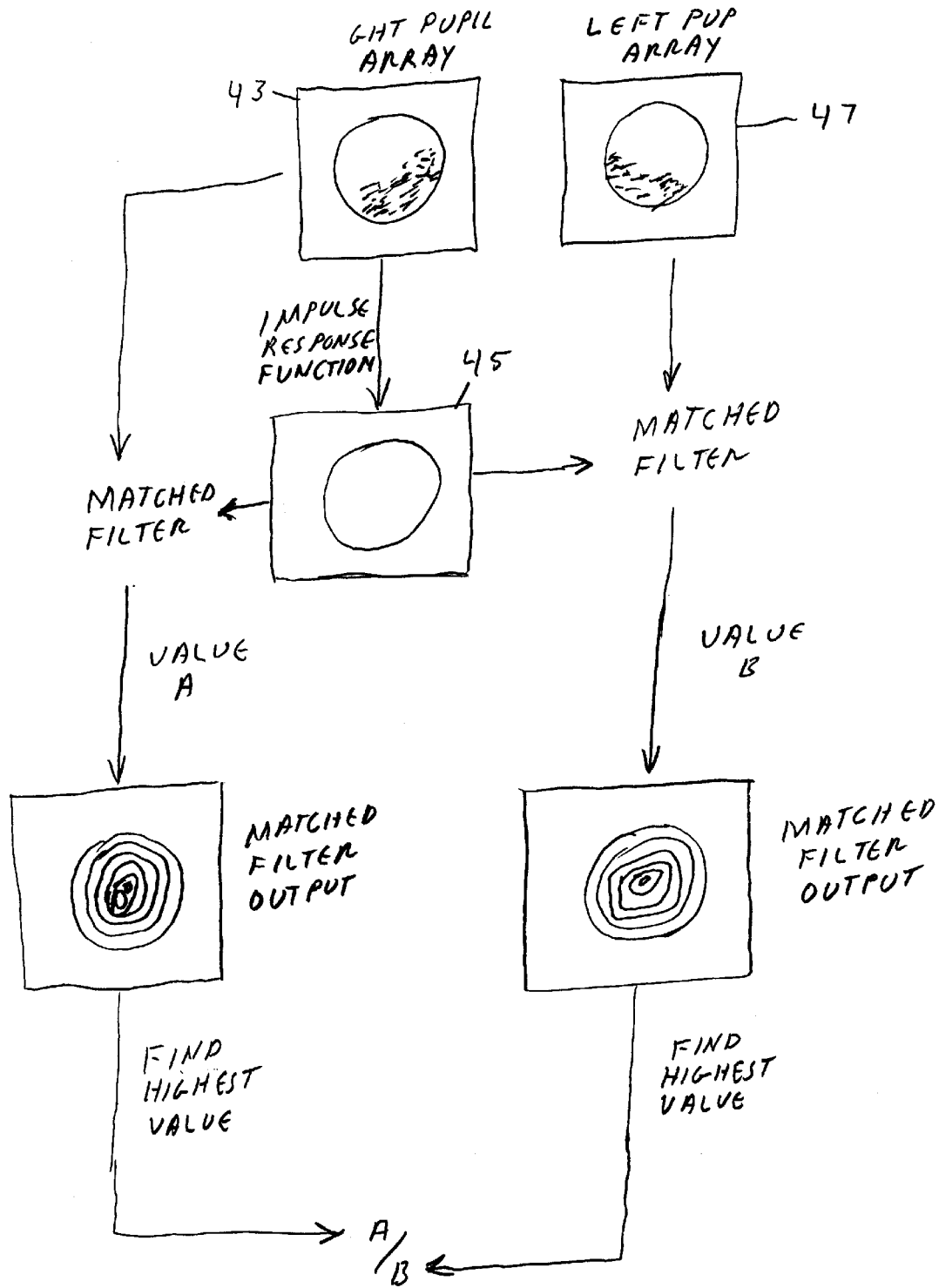
FIG. 8a is a diagram of the logic flow of FIG. 8.

FIG. 8 is a flowchart of a method for determining normalcy of balance between the eyes, this balance we call inter-symmetry. In this method, and at box 106, a pupil array 43 (FIG. 8*a*) of one of the eyes is retrieved. An impulse response function 45 is derived at box 108, and at box 110 the pupil array 43 and impulse response function 45 are applied to a matched filter to derive a highest correlation value A, which is stored. The pupil array 47 of the other eye is retrieved at box 114, and at box 116 the impulse response function 45 and pupil array 47 are applied to a matched filter to obtain a highest correlation value B. This B value is stored at box 118, and at box 120 the B value is divided by the A value. If the resulting number is greater than 1, then the A and B values at box 120 are inverted. The number resulting from these calculations is the inter-symmetry value. This inter-symmetry value measures how similar the eyes are with respect to each other. If the intensity distributions of the pupils are similar, then the inter-symmetry value will be near 1, indicating that the eyes are relatively balanced in power and lack significant cataracts or astigmatism. On the other hand, if the inter-symmetry value is significantly less than 1, then the eyes are significantly different in optical power, may have cataracts, astigmatism or other defects. Where a refined inter-symmetry value is desired, the exact circular pupils may be cropped from the array and normalized by the integral of its intensity distribution.

In the analysis of eyes of a subject, it has become apparent that strabismus, amblyopia, anisometropia and other conditions often share a coincidence of imbalance either into or out of the visual/motor centers of the brain. As such, several optical parameters of sensory and motor imbalance exist within the binocular retinal reflexes that may be extracted statistically in order to determine a visual/motor homeostasis of the individual being tested. This homeostasis is an optical manifestation that exists between the binocular stimulus and the neural-motor response of the subject to that stimulus. While always present in a binocular image of the eyes taken by a reflex photometer, homeostasis of the eyes of a subject may be obscure, necessitating statistical analysis, pattern recognition and other image enhancements in order to assess its state. At this time, about 40 statistical parameters in diagnostic algorithms are used to calculate a unique and characteristic expression that correlates with a corresponding disease process. For example, the degree of variance of pixel brightness in the reflex image between eyes may be used to predict certain disease processes. Here, eyes that are perfect or have 20/20 vision have very little variation of pixel brightness, i.e. are very uniform. On the other hand, pairs of eyes that are amblyopic have one eye that is brighter in about 92% of cases tested. In pairs of eyes that are anisometropic, the eye with greater optical power had a greater pixel intensity in 100% of cases tested. As such, the greater the variance of pixel intensity the greater the probability of eye misalignment and/or mismatched refractive error. It is expected that statistical measurements of the pupillary reflexes from pairs of eyes are likely to lead to other algorithms, in addition to the algorithms of FIGS. 7, 7a, 8, and 8a, that correlate the statistical measurements with clinical conditions of ocular imbalance.

A paper submitted by Applicants on approximately Apr. 16, 2000, is presented herein as Appendix A, this paper illustrating other features related to homeostatic analysis of the eyes.

Having thus described my invention and the manner of its use, it should be apparent to one skilled in the art that incidental changes may be made thereto that fairly fall within the scope of the following appended claims.

What is claimed is:

1. A method for analyzing a retinal reflection from at least one eye of a subject comprising the steps of:
    a) locating an image of an eye of a subject,
    b) applying a plurality of matched filter tests to selected portions of said image of an eye in order to locate at least an iris and pupil in said image of an eye,
    c) performing a plurality of intensity shape determination tests on said retinal reflection,
    d) performing a Hirshberg deviation test on said retinal reflection,
    e) performing symmetry tests on the intensity distribution of the retinal reflection,
    f) indicating a result.

2. A method as set froth in claim 1 further comprising the step of performing said matched filter tests and said intensity shape determination tests when said image of an eye is of low contrast.

3. A method as set forth in claim 1 wherein said step of applying a plurality of matched filter tests further comprises the step of testing different structures in the image of the eye.

4. A method as set forth in claim 3 wherein one of said matched filter tests is weighed toward matching to the iris ring, and comprises the steps of:
    a) thresholding said image of an eye so that pixels of said image having a value above said threshold are assigned a first binary value and pixels of said image having a value below said threshold are assigned a second binary value,
    b) performing an impulse response operation to develop a binary mask of said image of an eye,
    c) inverting both the image of an eye and said binary mask to develop an inverted image of an eye and an inverted binary mask,
    d) applying said inverted image of an eye and said inverted binary mask to a matched filter,
    e) obtaining a highest correlation from said matched filter.

5. A method as set forth in claim 3 wherein said step of performing a plurality of matched filter tests further comprises the steps of:
    a) performing an impulse response operation to develop a binary mask of said image of an eye,
    b) dividing said binary mask into first and second portions,
    c) comparing said first portion with a corresponding portion of said image of an eye,
    d) comparing said second portion with a corresponding portion of said image of an eye,
    e) obtaining a correlation from said comparisons of said first and second portions with a respective said corresponding portion of said image of an eye.

6. A method as set forth in claim 1 further comprising the step of determining hyperopia or myopia by applying a least squares fit to selected groupings of pixels making up said image of an eye.

7. A method as set forth in claim 6 wherein said step of applying a least squares fit further includes the step of applying said least squares fit to first order and second order polynomials of rows of pixels making up said image of an eye and columns of pixels making up said image of an eye.

8. A method as set forth in claim 7 further comprising the step of performing a linear fit to said retinal reflection, defining a slope of an intensity distribution of said retinal reflection.

9. A method as set forth in claim 7 further comprising the step of performing a quadratic fit to said retinal reflection, defining a curve of an intensity distribution of said retinal reflection.

10. A method as set forth in claim 1 further comprising the step of calculating a set of scalar parameters descriptive of said image of an eye, and utilizing said scalar parameters to determine selected features of said eye.

11. A method as set forth in claim 10 wherein said step of calculating a set of scalar parameters further comprises the step of calculating moments of Hu of an intensity distribution of said retinal reflection in order to determine shape of an intensity distribution of said image of an eye.

12. A method as set forth in claim 11 further comprising the step of converting said moments of Hu to Zernike polynomials prior to determining said shape of said intensity distribution.

13. A method as set forth in claim 1 further comprising the steps of:
    a) locating a corneal spike,
    b) locating a center of said retinal reflection,
    c) determining a distance between said center of said retinal reflection and said corneal spike,
    d) associating said distance with magnitude of deviation.

14. A method as set forth in claim 13 further comprising the steps of:
    a) determining an angle between said corneal spike and said center of said retinal reflection,
    b) associating said angle with direction of said deviation.

15. A method as set forth I claim 1 wherein said step of performing symmetry tests further comprises the steps of:
    a) selecting at least one axis of said retinal reflection, said axis dividing said reflex into first and second portions, said first and second portions being symmetrical, b) correlating an intensity distribution of pixels in said first portion to an intensity distribution of pixels in said second portion to determine symmetry of said intensity distribution within said reflex.

16. A method as set forth in claim 15 wherein said step of selecting at least one axis further comprises the steps of:
   a) developing a mirror image of said retinal reflection,
   b) developing an impulse response array from said mirror image,
   b) developing an impulse response array of said retinal reflection,
   c) applying said impulse response array from said mirror image to a matched filter to obtain a mirror image matched filter result,
   d) applying said impulse response array from said retinal reflection to said matched filter to obtain a retinal reflection matched filter result,
   e) comparing said mirror image matched filter result with said retinal reflection matched filter result to indicate symmetry of said retinal reflection.

17. A method as set forth in claim 1 wherein said step of performing symmetry tests further comprises the steps of:
   a) developing a first impulse response function of a said first retinal reflection from a first eye,
   b) applying said first impulse response function and said retinal reflection from said first eye to a matched filter to obtain a highest first matched filter result,
   c) applying a second retinal reflection from a second eye and said first matched filter result to a second matched filter to obtain a highest second matched filter result,
   d) comparing highest values of said first matched filter result and said second matched filter result to obtain an indication of similarity between said first retinal reflection and said second retinal reflection.

* * * * *